(12) United States Patent
Chenger et al.

(10) Patent No.: US 10,363,113 B1
(45) Date of Patent: Jul. 30, 2019

(54) ADJUSTABLE CONTAINMENT SHIELD

(71) Applicants: Joseph Chenger, Nashville, TN (US);
Paul Yahnian, Nashville, TN (US)

(72) Inventors: Joseph Chenger, Nashville, TN (US);
Paul Yahnian, Nashville, TN (US)

( * ) Notice: Subject to any disclaimer, the term of this patent is extended or adjusted under 35 U.S.C. 154(b) by 33 days.

(21) Appl. No.: 15/246,995

(22) Filed: Aug. 25, 2016

Related U.S. Application Data

(63) Continuation-in-part of application No. 13/742,587, filed on Jan. 16, 2013, now Pat. No. 9,427,288.

(51) Int. Cl.
*A61B 90/00* (2016.01)
*A61B 50/30* (2016.01)

(52) U.S. Cl.
CPC .............. *A61B 90/05* (2016.02); *A61B 50/30* (2016.02)

(58) Field of Classification Search
CPC ............ A61F 2013/00297; A61F 2013/00306; A61M 2025/0273; A61M 25/02; C11C 5/006; A61B 19/081; A61B 19/10; A61B 19/42
See application file for complete search history.

(56) References Cited

U.S. PATENT DOCUMENTS

| | | | | |
|---|---|---|---|---|
| 2004/0097996 A1* | 5/2004 | Rabiner | ........... | A61B 17/22012 606/159 |
| 2010/0024745 A1* | 2/2010 | Harlow | ................ | A01K 13/006 119/856 |
| 2011/0277701 A1* | 11/2011 | King | .................... | A01K 13/006 119/815 |

* cited by examiner

*Primary Examiner* — Ashley L Fishback
(74) *Attorney, Agent, or Firm* — Ryan D. Levy; Patterson Intellectual Property Law, P.C.

(57) ABSTRACT

An adjustable containment shield is operable to mount on an output housing of a surgical instrument. The shield includes a substantially transparent body including a distal face, a proximal face opposite the distal face, a generally consistent thickness defined between the distal face and the proximal face such that the body is pliable and resilient, a mounting hole defined in the body to engage the output housing, and a plurality of folds to allow the shield to move from a retracted position to an expanded position. When mounted on the output housing, the distal face is at an acute angle with respect to a longitudinal axis through the mounting hole and face is also facing toward a patient engagement end of the surgical instrument. The proximal face is at an obtuse angle with respect to the longitudinal axis and facing toward a housing side of the surgical instrument.

19 Claims, 11 Drawing Sheets

ADJUSTABLE CONTAINMENT SHIELD

CROSS-REFERENCES TO RELATED APPLICATIONS

This application is a continuation-in-part of parent application Ser. No. 13/742,587 filed on Jan. 16, 2013, entitled CONTAINMENT SHIELD FOR SURGICAL INSTRUMENTS, the contents of which are hereby incorporated by reference.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND

The present disclosure relates to containment shields. More particularly, the disclosure pertains to an adjustable containment shield operable to mount on an output housing of a surgical instrument that generates debris.

Orthopedic surgery often involves cutting hard biological tissues such as bone or cartilage. Orthopedic surgeons frequently use power tools to increase the speed and accuracy of surgical procedures, which results in better patient outcomes. These power tools often include surgical instruments such as saws, drills, chisels, pneumatic hammers, grinders, cutting wheels, and rotary cutting tools (e.g., a Dremel™ tool). These and other surgical instruments cause spatter of biological material including blood, bone fragments, soft tissue, etc. To prevent the spread of disease, patients are covered in gowns and/or surgical drapes. Machines in the operating room may also be covered with surgical drapes, and orthopedic surgeons and other surgical personnel wear full surgical outfits including a gown, gloves, a hat, and a face shield. The surgeon, a nurse, or other operating room personnel must frequently clean the orthopedic surgeon's face shield to maintain visibility while the surgeon is using a surgical instrument. Even with frequent cleaning, visibility is often reduced due to inadequate cleaning. This issue slows down orthopedic surgical procedures and may negatively impact surgical outcomes. Furthermore, the use of instruments for orthopedic surgery may result in spatter of biological material in a large area within an operating room. This spatter can further complicate the surgical procedure as well as the subsequent cleaning of the operating room.

Additionally, the spattered material may rebound off of one or more items it impacts, particularly if the spattered material is a bone fragment. Thus, even with current protective gear in use, it is possible for operating room personnel to be contaminated by spattered material (e.g., material bouncing off of a face shield into an eye of someone in the operating room, ejected material during the procedure landing on a sterile field causing contamination or infection, or ejected material landing on and contaminating personnel in the operating room). Further, this rebounding effect can leave an operating room spattered not only on equipment and personnel facing the patient or the subject, but also on the back, top, and underside of the equipment and personnel in the operating room. The operating room can, therefore, become very messy, and cleaning can become very time consuming. Additionally, secondary contamination can result from drippings off the ceiling or other areas and can possibly infect a current or subsequent patient as well as spread body fluids and contaminants to nearby personnel. Other doctors, patients, and support staff may run the risk of being contaminated with infectious pathogens and the like.

BRIEF SUMMARY

In one embodiment, the adjustable containment shield is operable to mount on an output housing of a surgical instrument. The containment shield includes a substantially transparent body. The body includes a distal face, a proximal face opposite the distal face, a generally consistent thickness defined between the distal face and the proximal face such that the body is pliable and resilient, a mounting hole defined in the body and operable to engage the output housing of the surgical instrument, and a plurality of folds configured to allow the containment shield to move from a retracted position to an expanded position. When mounted on the output housing of the surgical instrument, the distal face is at an acute angle with respect to a longitudinal axis through the mounting hole. The distal face is also facing toward a patient engagement end of the surgical instrument in such a configuration. The proximal face is at an obtuse angle with respect to the longitudinal axis. The proximal face is also facing toward a housing side of the surgical instrument in such a configuration.

In one aspect, the body further includes an outer edge and a plurality of facets defined on the proximal face. Each facet is bounded by respective folds and the outer edge. At least one facet is configured to pivot relative to the mounting hole such that the containment shield moves from the retracted position to the expanded position.

In another aspect, the body further includes a plurality of accordion sections. Each accordion section includes alternating adjacent folds of the plurality of folds, such that the at least one facet may pivot relative to the mounting hole.

In still another aspect, the body further includes two accordion sections.

In yet another aspect, the body further includes four accordion sections.

In a further aspect, the plurality of facets includes insert facets, and the plurality of facets form guides. Each guide is configured to slidably receive a respective insert facet of the plurality of facets, such that the at least one facet may pivot relative to the mounting hole.

In another further aspect, the containment shield further includes a package. The plurality of folds in the body of the containment shield enable the package to maintain the containment shield substantially flat within the package, and the containment shield is sterile within the package.

In yet a further aspect, the containment shield further includes a collar operable to connect the mounting hole of the body to the output housing of the surgical instrument.

In still a further aspect, the body further includes a plurality of slits therethrough. Each slit of the plurality of slits extends radially from a center point of the mounting hole.

In a further still aspect, the body further includes a plurality of slits therethrough. Each slit of the plurality of slits extend perpendicularly from an edge of the mounting hole.

In another aspect, the body further includes a reflection reducing coating.

In some aspects, the mounting hole is operable to receive a shaft of the surgical instrument. The containment shield may be mounted such that it prevents unwanted transmission of fluids or other contaminants. The containment shield further includes a removable layer of film on the distal face of the body. The removable layer of film includes a peel tab protruding from an edge of the body.

In other aspects, the mounting hole has a diameter of approximately one half of an inch or larger. The body further includes a plurality of slits therethrough. Each slit of the plurality of slits extends from an edge of the mounting hole. Each slit has a length of approximately one half of an inch.

In an embodiment, a method of using an adjustable containment shield operable to mount on an output housing of a surgical instrument is disclosed. The method includes forming the containment shield into a three-dimensional shape including a distal face and a proximal face; engaging a mounting hole of the containment shield onto the output housing of the surgical instrument such that the distal face is at an acute angle with respect to a longitudinal axis through the mounting hole and facing toward a patient engagement end of the surgical instrument while the proximal face is at an obtuse angle with respect to the longitudinal axis and facing toward a housing side of the surgical instrument; and pivoting a facet of the containment shield relative to the mounting hole, thereby moving the containment shield from a retracted position to an extended position.

In an aspect, pivoting the facet of the containment shield includes extending a plurality of accordion sections.

In another aspect, pivoting the facet of the containment shield includes sliding an insert facet relative to a respective guide.

In yet another aspect, the method further includes removing a removable layer of film from the distal face. The removable layer of film includes a peel tab protruding from an edge of the distal face.

In still another aspect, the method further includes removing the containment shield from packaging. The containment shield includes a body that is substantially transparent and has a generally consistent thickness such that the body is pliable and resilient. The body is substantially planar when in the packaging.

In a further aspect, forming the containment shield into a three-dimensional shape further includes creating a plurality of folds configured to allow the containment shield to move from the retracted position to the expanded position.

In still a further aspect, the method further includes pivoting the facet of the containment shield relative to the mounting hole, thereby moving the containment shield from the extended position to the retracted position.

Aside from the structural and procedural arrangements set forth above, the invention could include a number of other arrangements, such as those explained hereinafter. It is to be understood, that both the foregoing description and the following description are exemplary.

The accompanying drawings are incorporated in and constitute a part of the specification. The drawings illustrate optional embodiments of the invention and together with the description serve to explain some principles of the invention.

BRIEF DESCRIPTION OF THE SEVERAL VIEWS OF THE DRAWINGS

Reference will now be made in detail to optional embodiments of the invention, examples of which are illustrated in accompanying drawings. Whenever possible, the same reference numbers are used in the drawings and in the description referring to the same or like parts.

DETAILED DESCRIPTION

Figure 1A:
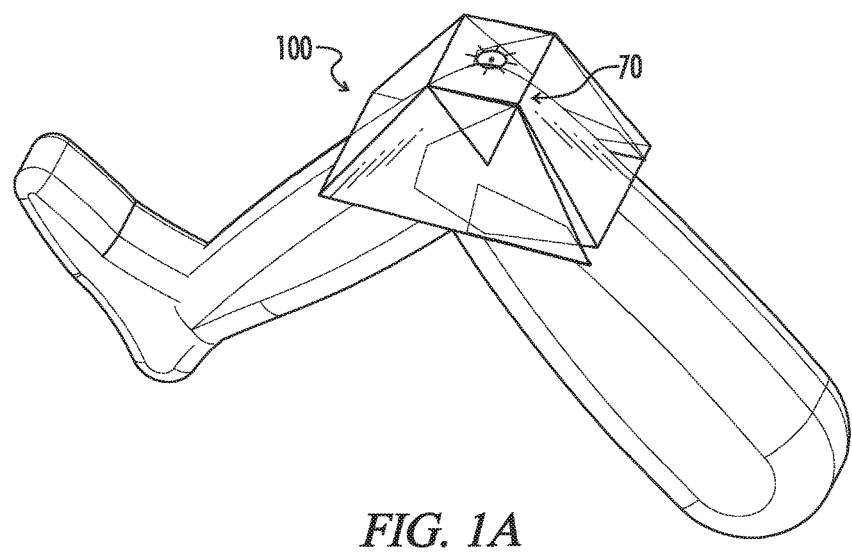
FIG. 1A is a perspective view of an embodiment of an adjustable containment shield in a retracted position while placed on a knee when the knee is bent.

While the making and using of various embodiments are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements, and/or states are in any way required for one or more embodiments.

To the extent that the term "includes" or "including" is used in the specification or the claims, it is intended to be inclusive in a manner similar to the term "comprising" as that term is interpreted when employed as a transitional word in a claim. Furthermore, to the extent that the term "or"

is employed (e.g., A or B) it is intended to mean "A or B or both." Furthermore, to the extent the term "connect" is used in the specification or claims, it is intended to mean not only "directly connected to," but also "indirectly connected to" such as connected through another component or multiple components.

To facilitate the understanding of the embodiments described herein, a number of terms are defined below. The terms defined herein have meanings as commonly understood by a person of ordinary skill in the areas relevant to the embodiments described herein. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

As used herein, "fold" is intended to refer to a fold, crease, or other joint. Furthermore, as used herein, the term "containment shield" includes, but is not limited to, embodiments that contain elements during surgical procedures or the like. This can include fluids, debris, smoke, certain wavelengths of light, biologic, and non-biologic material. The term "containment shield" can also be understood as a device that at least partially assists in blocking spatter, which may include the splashing or impact of biological and non-biological material against the shield.

Also as used herein, "hole" is intended to refer to any opening in the adjustable containment shield. The "hole" may be any configuration of an opening, gap, aperture, slit, slot, split, orifice, break, cut, space, perforation, puncture, notch, passage, vent, tear, window, mouth, cut, break, and the like. The "hole" may also include a plurality of holes instead of just one. The "hole" may have a jagged or smooth periphery and may or may not include slots. The "hole" may be of any appropriate shape including, for instance, square, circular, octagonal, rectangular, elliptical, trapezoidal, and the like.

As used herein, "surgical instrument" is intended to refer to any appropriate tool to be used on a patient, animal, or cadaver in human or veterinary surgery, organ harvesting, or autopsy. Particularly relevant are "surgical instruments" that may result in spatter or release of biological material. Such "surgical instruments" may include needles, saws, lasers or laser cutting tools, laser coagulators, grinders, knives, scalpels, screwdrivers, chisels, forceps, clamps, hooks, dental tools, irrigation tools, suction tools, drills, hammers, cutting wheels, cauterizing devices, water pulsating devices, rasps, pliers, organ harvesting tools, tissue harvesting tools, impactors, a rotary cutting tool such as a Dremel™ tool and the like. Such surgical instruments may be used primarily on biological tissue (e.g., removing bone spurs, fragments, etc.) or on foreign objects (e.g., screws, plates, wires, fusion devices, etc.).

Further, as used herein, "biological material" is intended to refer to any number of solids, liquids, gases, suspensions, spatters, aerosols, and the like. "Biological material" may include blood, bone fragments, soft tissue, cartilage, pathogens, parasites, puss, smoke, ground bone dust, burned tissue smoke, aerosolized liquids, saliva, tendons, blood vessels, muscle tissue, and the like.

Figure 6:
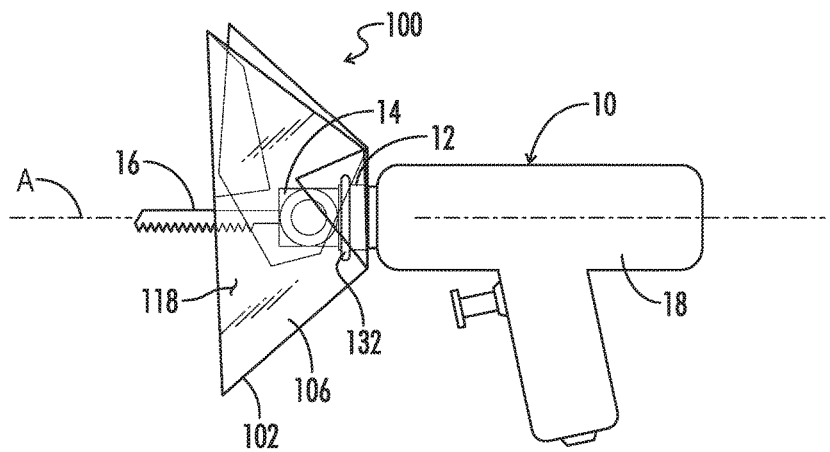
FIG. 6 is a side elevation view of the adjustable containment shield of FIG. 1A paired with a surgical instrument.
Figure 7:
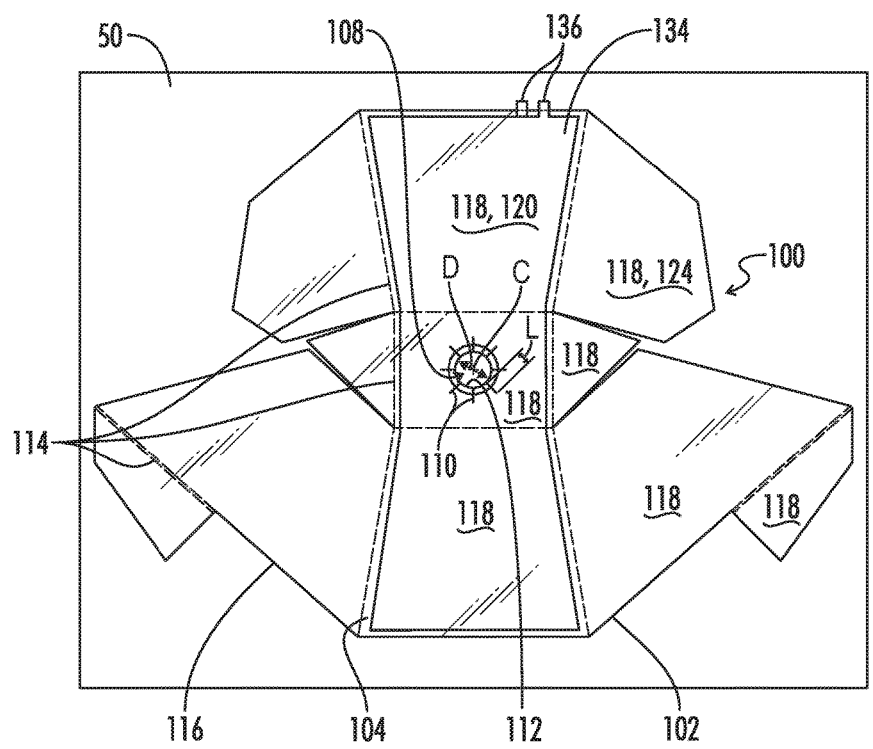
FIG. 7 is a top plan view of the adjustable containment shield of FIG. 1A laid flat in sterile packaging.
Figure 8A:
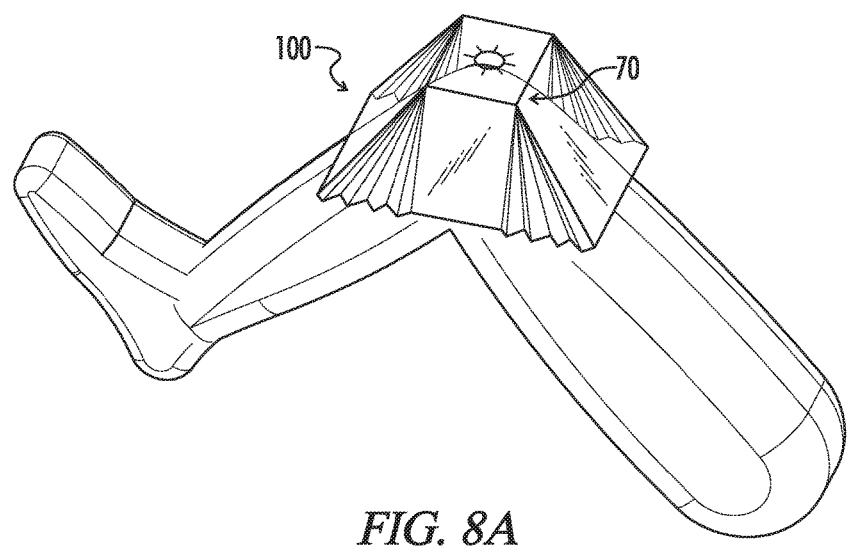
FIG. 8A is a perspective view of another embodiment of an adjustable containment shield in a retracted position while placed on a knee when the knee is bent.
Figure 8B:
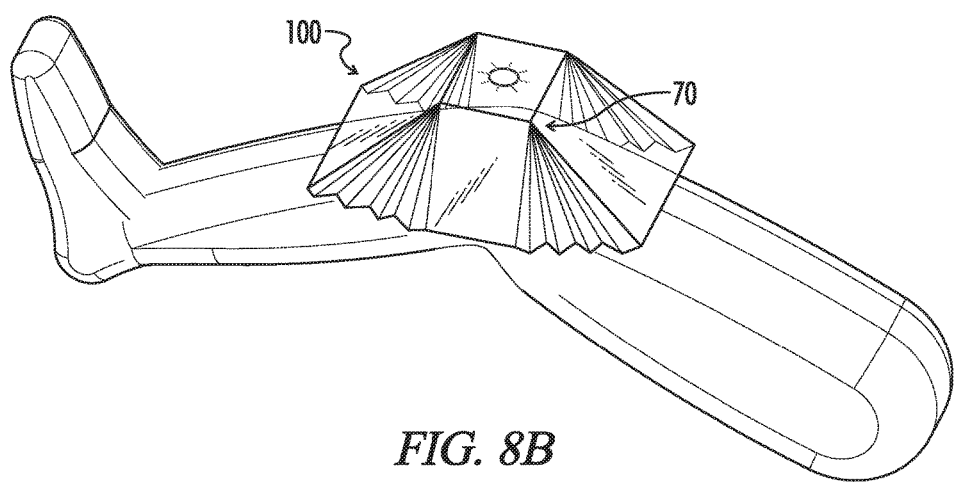
FIG. 8B is a perspective view of the adjustable containment shield of FIG. 8A in an expanded position while placed on the knee when the knee is straighter.

Referring to FIG. 6, an adjustable containment shield 100 is operable to mount on a surgical instrument 10. Particularly, the adjustable containment shield 100 is operable to mount on an output housing 12 of the surgical instrument 10. As shown in FIGS. 2A-5, the adjustable containment shield 100 includes a body 102 having a distal face 104 and a proximal face 106. The body 102 may be substantially transparent and may have a generally consistent thickness defined between the distal face 104 and the proximal face 106 such that the body is pliable and resilient. Optionally, the thickness may range from about 0.005 inches to about 0.05 inches thick with many optional embodiments being around 0.015 inches thick. Optionally, the thickness may depend on the specific application for which the adjustable containment shield 100 will be used. The stated thickness range is only an example, and in some optional embodiments, the body 102 may be thicker or thinner. In one embodiment, the body 102 includes a reflection reducing coating. In another embodiment, the body 102 is formed from a reflection reducing or non-reflective material. The adjustable containment shield 100 may have a generally rectangular outline when flattened. Other outline shapes, including the one shown in FIG. 7, are contemplated to be within the scope of the claims.

The body 102 may also include a mounting hole 108 defined therein. The mounting hole 108 may be operable to engage the output housing 12 of the surgical instrument 10. In some embodiments, a shaft 14 of the surgical instrument 10 may pass through the mounting hole 108 together with a portion of the output housing 12 of the surgical instrument. A portion of the body 102 adjacent the mounting hole 108 may frictionally engage the output housing 12 of the surgical instrument 10.

A plurality of slits 110 may be defined through the body 102 and may extend from an edge 112 of the mounting hole 108. In one embodiment, each slit 110 extends radially from a center point C of the mounting hole 108. In another embodiment, each slit 110 extends perpendicularly from the edge 112 of the mounting hole 108. Some embodiments include a circular mounting hole 108 having a diameter D of approximately one half of an inch or larger. In such embodiments, each slit 110 may have a length L of approximately one half of an inch. Other embodiments may include a substantially square or rectangular mounting hole 108. Such a mounting hole 108 may be used to mount on a square or rectangular output housing 12. In one embodiment, the mounting hole 108 may be square with each side measuring 3/16 of an inch. The body 102 may have a width W of between approximately 8 and 10 inches. It is contemplated that these dimensions may vary to accommodate different sizes and types of surgical instruments 10. In an alternative embodiment, no slits 110 are defined in the body 102.

It is contemplated that an output housing 12 of a surgical instrument 10 may be generally integral with the housing of the surgical instrument. It is also contemplated within the scope of the disclosure that the mounting hole 108 may be any size or shape (e.g., square, circular, rectangular, or otherwise) so as to generally correspond to a class or type of surgical instrument 10. Further, the overall size of the adjustable containment shield 100 may vary according to the intended surgical instrument 10.

As shown in FIG. 7, the adjustable containment shield 100 may lay flat in a sterile package 50. Alternatively, the adjustable containment shield 100 may be folded over itself and lay flat in the sterile package 50. The sterile package 50 may maintain the adjustable containment shield 100 in a substantially flat configuration within the sealed sterile enclosure of the sterile package.

Figure 1B:
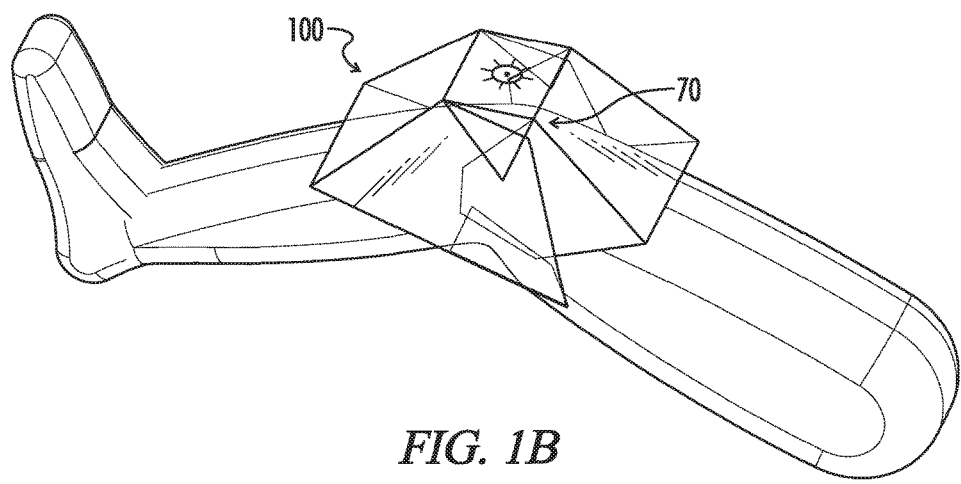
FIG. 1B is a perspective view of the adjustable containment shield of FIG. 1A in an expanded position while placed on the knee when the knee is straighter.

The body 102 of the adjustable containment shield 100 may further include a plurality of folds 114. The plurality of folds 114 may be configured to allow the adjustable containment shield 100 to move from a retracted position (shown in FIGS. 1A, 2A, and 3) to an expanded position (shown in FIGS. 1B, 2B, 4, and 5). The plurality of folds 114 may also allow the adjustable containment shield 100 to move from the expanded position to the retracted position. This adjustability from the expanded position to the retracted position (and vice-versa) allows the adjustable containment shield 100 to adequately surround the biological tissue in a variety of positions. For instance, a patient's knee 70 may need to be extended (as shown in FIG. 1B) during a portion of the surgical procedure and bent (as shown in FIG. 1A) during another portion of the surgical procedure. As such, the adjustable containment shield 100 may substantially surround the knee 70 no matter the knee's orientation.

Returning to FIGS. 2A-5, the adjustable containment shield 100 may also include the body 102 further including an outer edge 116 and a plurality of facets 118 defined on the proximal face 106. The plurality of facets 118 may also be defined on the distal face 104. Each facet 118 may be bounded by respective folds 114 and the outer edge 116. At least one facet 118, a pivot facet 120, may be configured to pivot relative to the mounting hole 108 such that the adjustable containment shield 100 moves from the retracted position to the expanded position.

In one embodiment (shown in FIGS. 8A-11), the body 102 further includes a plurality of accordion sections 122. Each accordion section 122 may include alternating adjacent folds 114 of the plurality of folds such that the at least one facet 118, or pivot facet 120, may pivot relative to the mounting hole 108. Some embodiments of the adjustable containment shield 100 may include the body 102 including two accordion sections 122. Other embodiments of the adjustable containment shield 100 may include the body 102 including four accordion sections 122.

In one embodiment (shown in FIGS. 1A-7), the plurality of facets 118 includes insert facets 124. The plurality of facets 118 may form guides 126. Each guide 126 may be configured to slidably receive a respective insert facet 124 of the plurality of facets 118 such that the at least one facet 118, or pivot facet 120, may pivot relative to the mounting hole 108. In a particular embodiment, the plurality of facets 118 may form lower guides 128 and upper guides 130. In such an embodiment, a respective insert facet 124 may be received between a lower guide 128 and an upper guide 130 such that the insert guide may slide relative to the guides 126.

In some embodiments (shown in FIGS. 6 and 10), the adjustable containment shield 100 further includes a collar 132. The collar 132 may be operable to connect the mounting hole 108 of the body 102 to the output housing 12 of the surgical instrument 10. The collar 132 may retain the mounting hole 108 of the body 102 on the output housing 12 of the surgical instrument 10. The collar 132 slips onto the output housing 12 after the adjustable containment shield 100 to prevent the adjustable containment shield from slipping down the output housing toward the patient engagement end 16. In another embodiment, the collar 132 slides onto the output housing 12 before the adjustable containment shield 100, and after the adjustable containment shield is installed on the output housing, the collar is slid over a portion of the body 102 adjacent the mounting hole 108 to increase the frictional engagement of the body to the output housing. In one embodiment, the collar 132 includes silicone rubber. The collar 132 may be turned inside out to roll down the output housing 12 onto the portion of the body 102 adjacent the mounting hole 108 (i.e., the portion free to lay flat against the output housing due to slits 110).

When the adjustable containment shield 100 is mounted on the output housing 12 of the surgical instrument 10, the distal face 104 of the body 102 is at an acute angle with respect to a longitudinal axis A through the mounting hole 108. The distal face 104 is also facing toward a patient engagement end 16 of the surgical instrument 10 when the adjustable containment shield 100 is mounted on the output housing 12. In such a configuration, the proximal face 106 of the body 102 is at an obtuse angle with respect to the longitudinal axis A. The proximal face 106 is also facing toward a housing side 18 of the surgical instrument 10.

Figure 11:
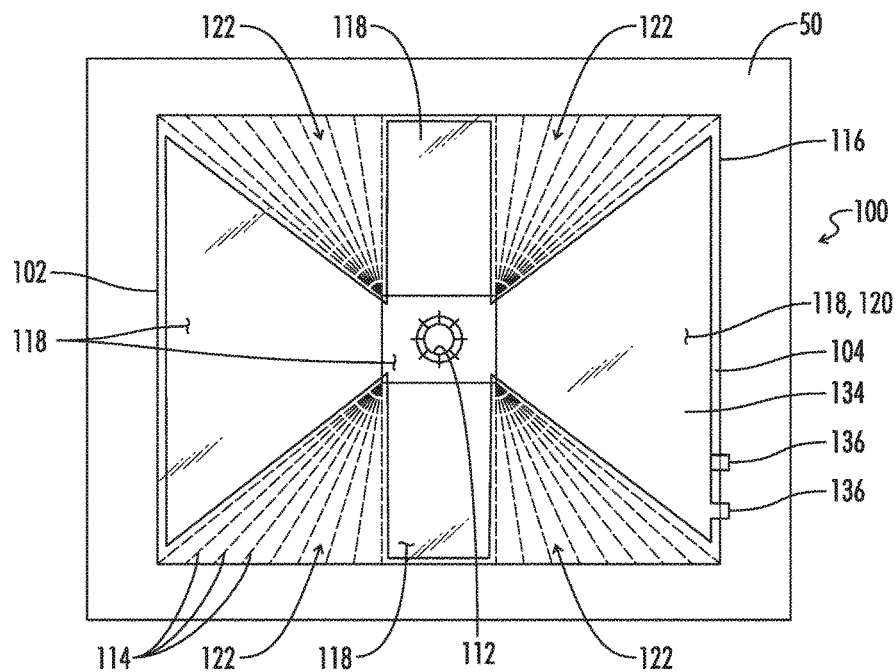
FIG. 11 is a top plan view of the adjustable containment shield of FIG. 8A laid flat in sterile packaging.

As shown in FIGS. 7 and 11, some embodiments of the adjustable containment shield 100 further include a removable layer of film 134 disposed on the distal face 104 of the body 102. The removable layer of film 134 may include a peel tab 136 protruding from an edge 112, 116 of the body 102. The adjustable containment shield 100 may include multiple removable layers of film 134 on the distal face 104. In one embodiment, the removable layer of film 134 is a thin layer of plastic adhered to the body 102 or underlying layer of film by static cling or a light duty adhesive. In one embodiment, the film 134 is 0.5 mil thick polyvinyl chloride (PVC). When visibility through the most distal layer of film 134 of the plurality of layers of film becomes obscured by spatter, operating room personnel can peel the layer of film from the adjustable containment shield 100, resulting in a substantially spatter-free adjustable containment shield. With each layer of film 134 including a peel tab 136, successive tabs corresponding to respective successively less distal layers of film may be adjacent the peel tab of the most distal layer of film. In one embodiment, the most distal layer of film 134 may include a slit therethrough from the outer edge 116 to the inner edge 112 of the mounting hole 108. The slit may allow the layer of film 134 to be peeled from the adjustable containment shield 100 with reduced interaction with the patient engagement end 16 of the surgical instrument 10, thereby aiding in prevention of injury to operating room personnel and/or the patient. Although the layer of film 134 is shown in FIGS. 7 and 11 as inset from the edges 112, 116 of the body 102, it is contemplated that the edges of the layer(s) of film may be inset or coextensive with the edges of the body.

Figure 2A:
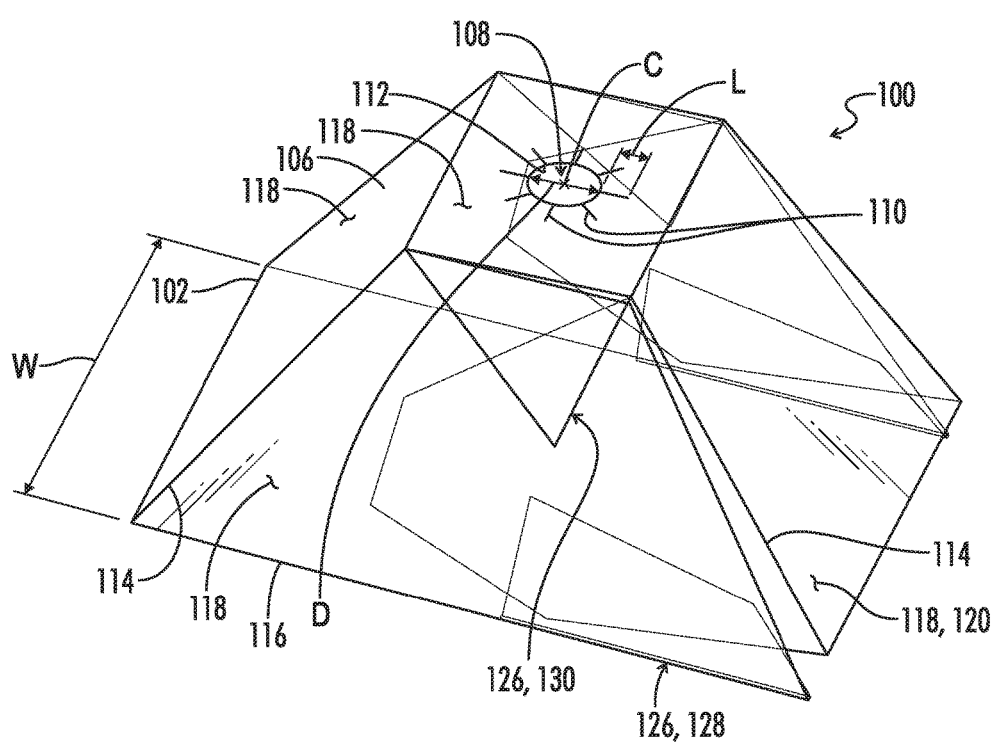
FIG. 2A is a perspective view of the adjustable containment shield of FIG. 1A in a retracted position.
Figure 2B:
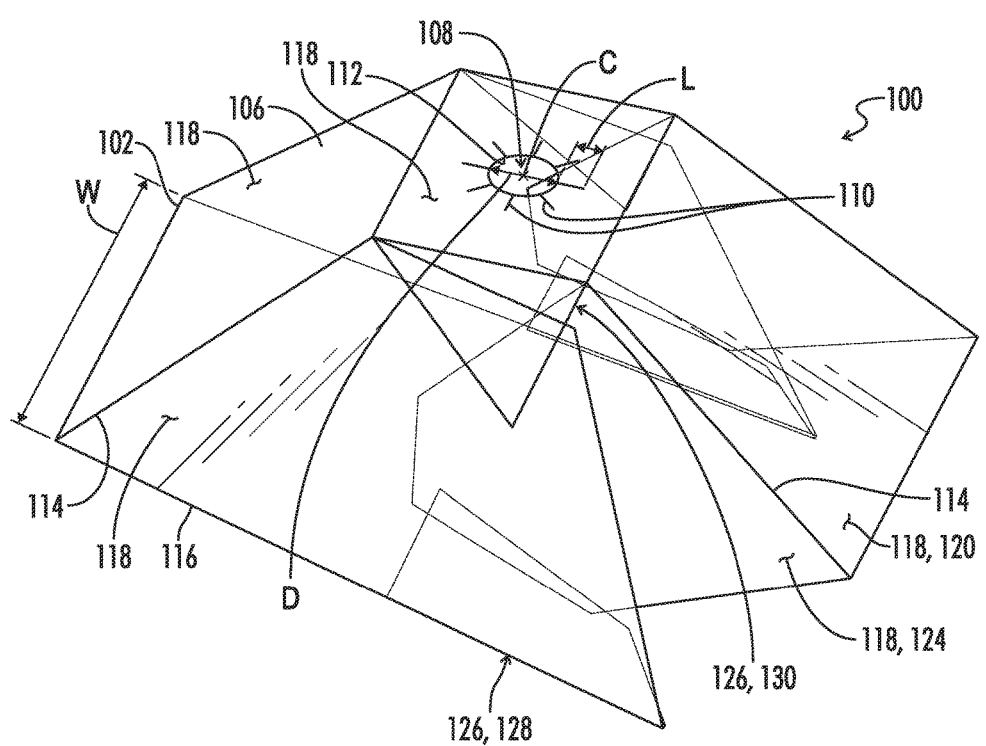
FIG. 2B is a perspective view of the adjustable containment shield of FIG. 1A in an expanded position.
Figure 3:
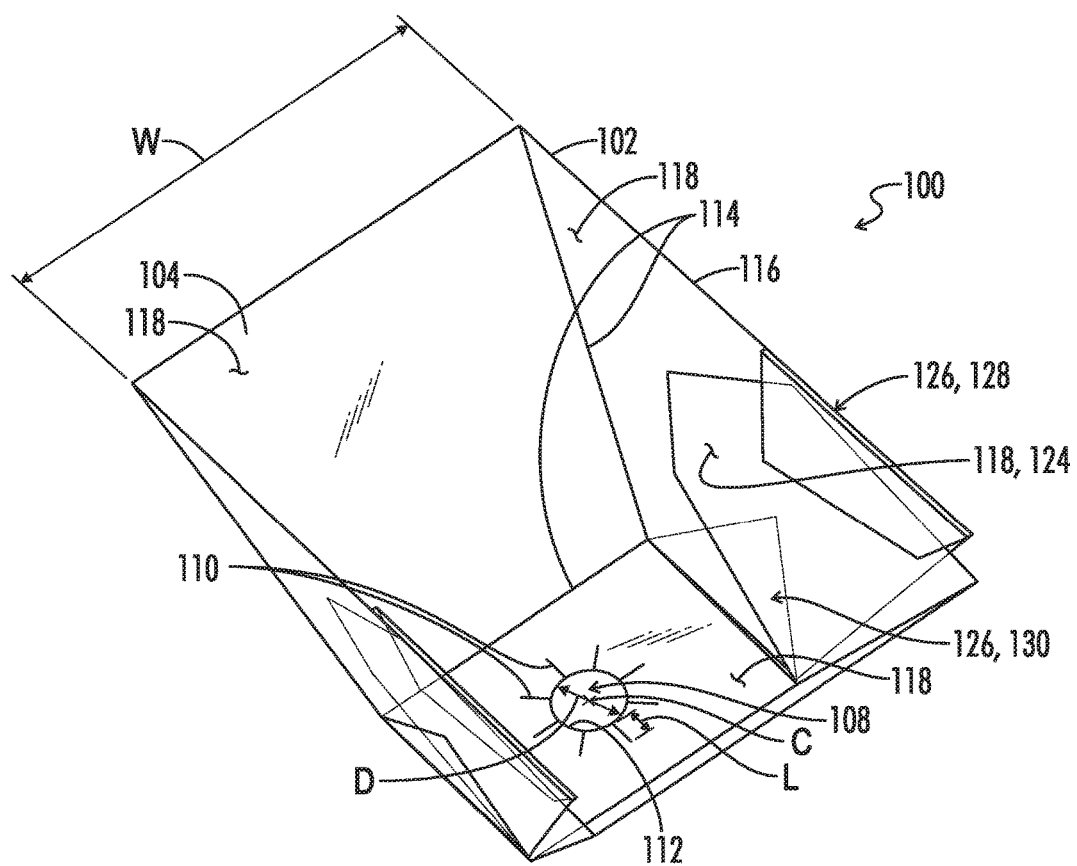
FIG. 3 is a bottom perspective view of the adjustable containment shield of FIG. 1A in the retracted position.
Figure 4:
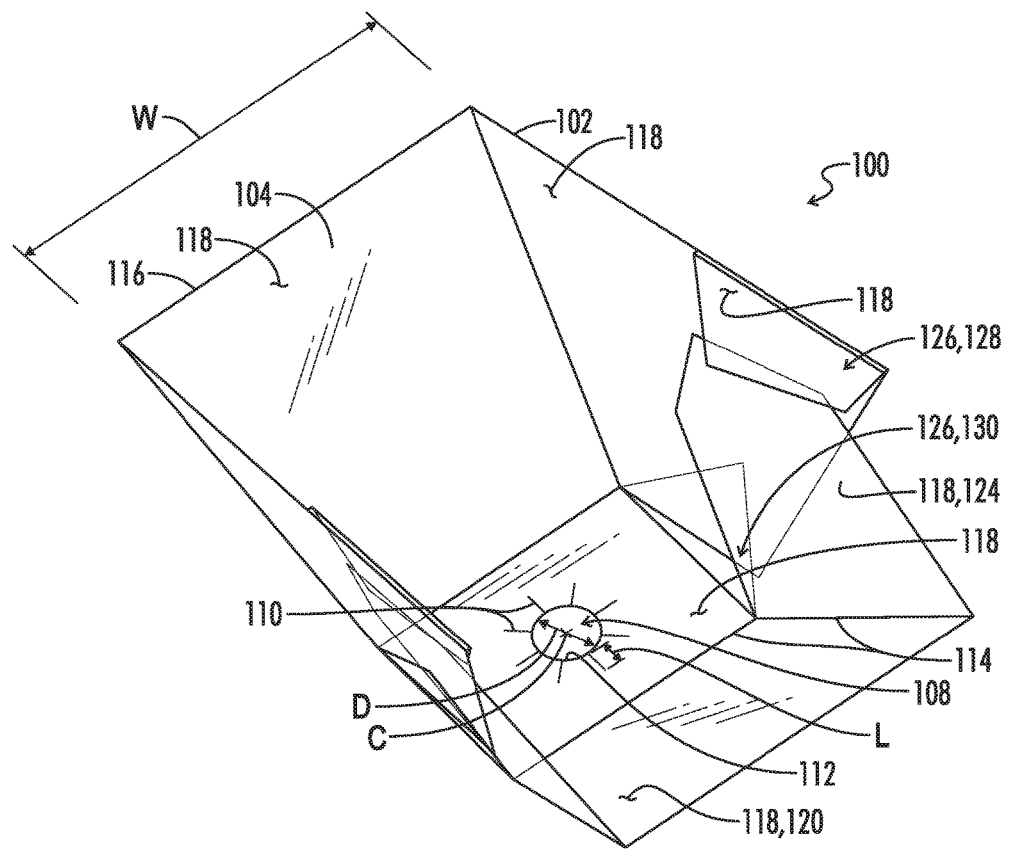
FIG. 4 is a bottom perspective view of the adjustable containment shield of FIG. 1A in an expanded position.
Figure 5:
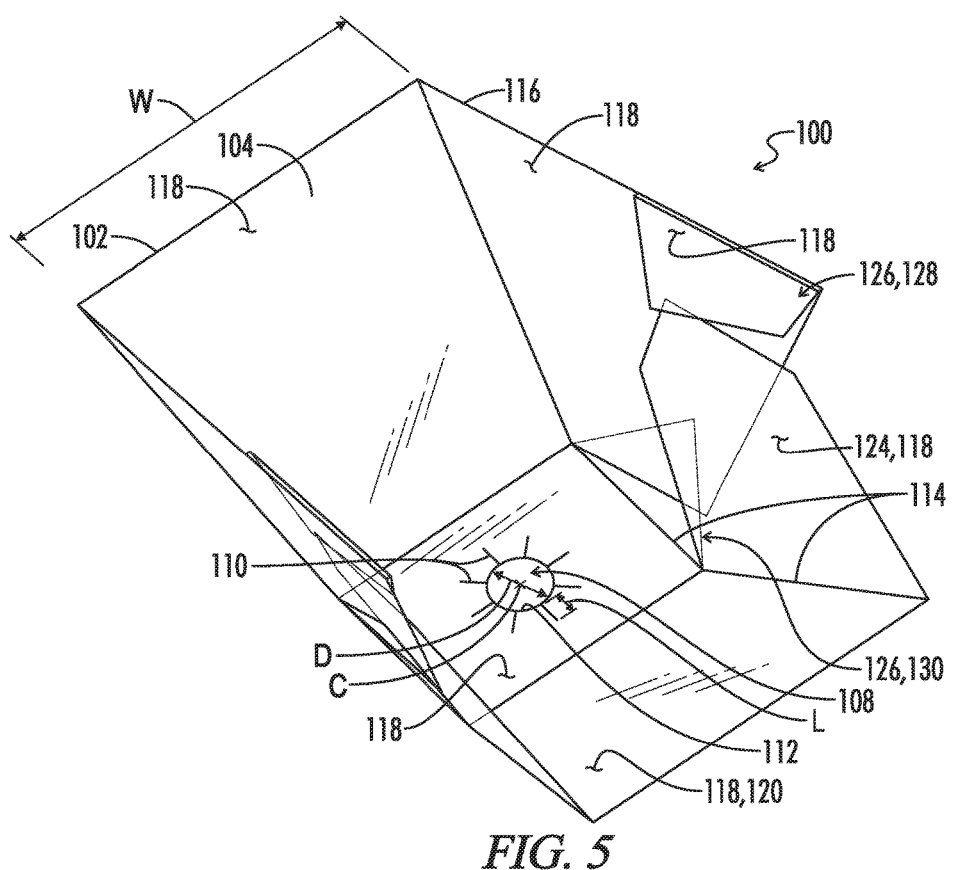
FIG. 5 is a bottom perspective view of the adjustable containment shield of FIG. 1A in a further expanded position.
Figure 9A:
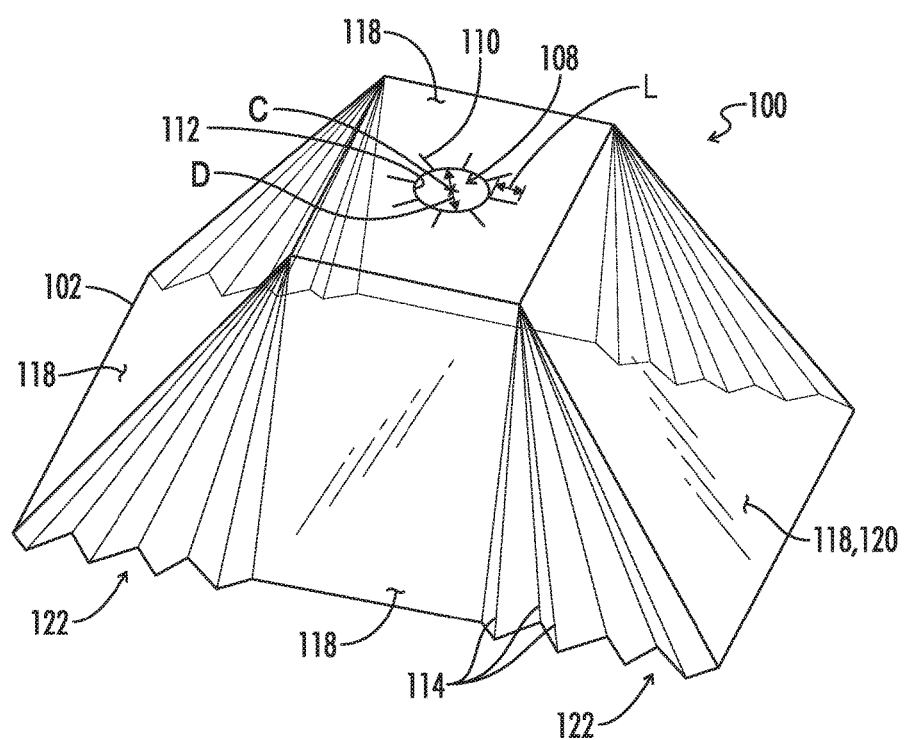
FIG. 9A is a perspective view of the adjustable container shield of FIG. 8A in the retracted position.
Figure 9B:
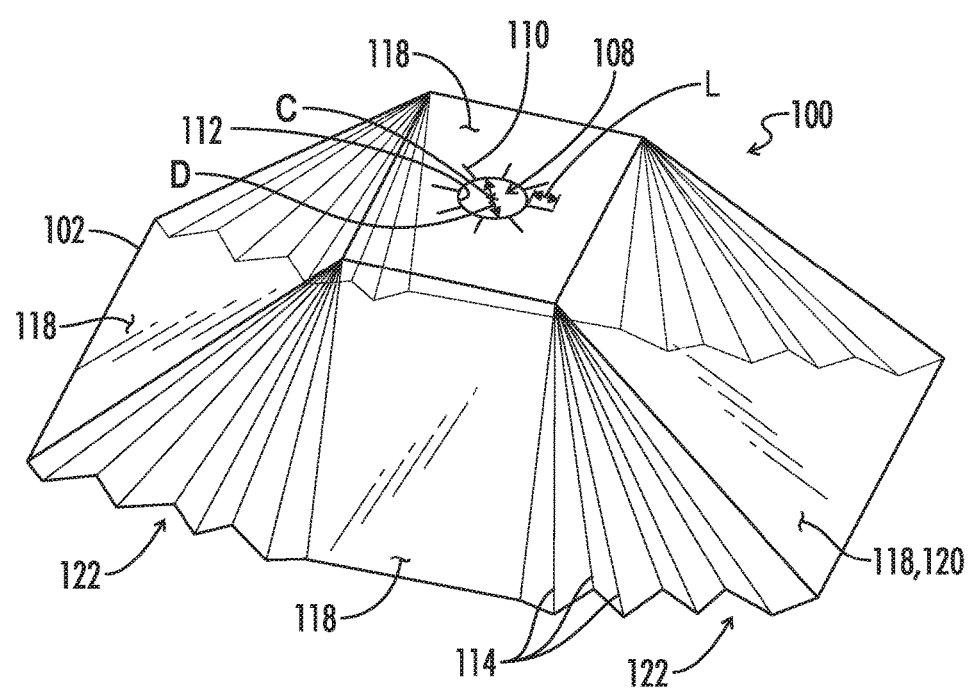
FIG. 9B is a perspective view of the adjustable container shield of FIG. 8A in the expanded position.
Figure 10:
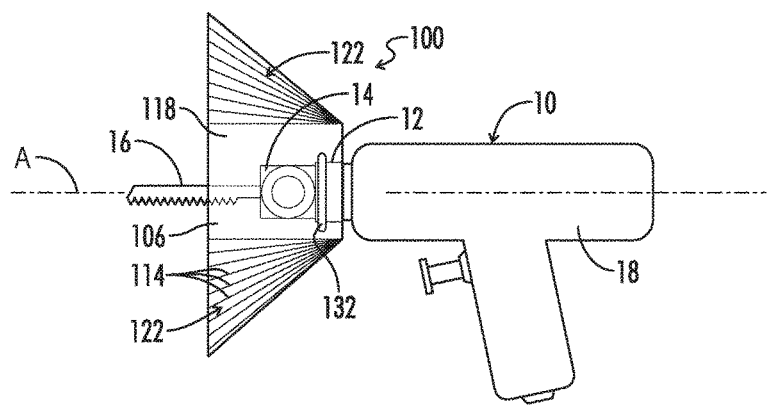
FIG. 10 is a side elevation view of the adjustable containment shield of FIG. 8A paired with a surgical instrument.

The present disclosure also relates to a method of using an adjustable containment shield 100. The adjustable containment shield 100 may be operable to mount on an output housing 12 of a surgical instrument 10. The method may include forming the adjustable containment shield 100 into a three-dimensional shape (as shown in FIG. 2A or 9A) including a distal face 104 and a proximal face 106. In some embodiments, the adjustable containment shield 100 may be substantially flat (or substantially planar) when contained within packaging 50 (as shown in FIG. 7 or 11). In such a method, the adjustable containment shield 100 may be removed from the packaging 50 prior to forming the adjustable containment shield into the three-dimensional shape. The method may further include engaging a mounting hole 108 of the adjustable containment shield 100 onto the output housing 12 of the surgical instrument 10. While the adjustable containment shield 100 is engaged onto the output housing 12, the distal face 104 may be at an acute angle with respect to a longitudinal axis A through the mounting hole 108 and facing toward a patient engagement end 16 of the surgical instrument 10 while the proximal face 106 is at an obtuse angle with respect to the longitudinal axis and facing toward a housing side 18 of the surgical instrument. The method may also include pivoting a facet 118, or pivot facet 120, of the adjustable containment shield 100 relative to the mounting hole 108, thereby moving the adjustable containment shield from a retracted position (shown in FIGS. 1A, 2A, and 3) to an extended position (shown in FIGS. 1B, 2B, 4, and 5). In some embodiments, pivoting the facet 118, or pivot facet 120, may include extending a plurality of accordion sections 122. In other embodiments, pivoting the facet 118, or pivot facet 120, may include sliding an insert facet 124 relative to a respective guide 126. In one embodiment, the method may further include removing a removable layer of film 134 from the distal face 104 of the body 102. The removable layer of film 134 may include a peel tab 136 protruding from an edge 112, 116 of the distal face 104. The step of forming the adjustable containment shield 100 into a three-dimensional shape may also include creating a plurality of folds 114 configured to allow the adjustable containment shield to move from the retracted position to the expanded position. The method may also include pivoting the facet 118, or pivot facet 120, of the adjustable containment shield 100 relative to the mounting hole 108, thereby moving the containment shield from the extended position to the retracted position. The method may further include operating the surgical instrument 10 to cut biological material (such as a patient's knee 70), and replacing the adjustable containment shield 100 with another adjustable containment shield (i.e., repeating the previous steps of the method) when visibility through the adjustable containment shield is reduced due to debris from cutting the biological material.

While the adjustable containment shield 100 is described as being used for surgical applications, particularly orthopedics, the device can also be used for a variety of other applications, as well. Various different medical procedures, dental surgery, veterinary medicine, organ transplants, organ harvesting, and also forensic applications are contemplated.

Additionally, while a variety of optional embodiments of the adjustable containment shield 100 include the adjustable containment shield formed from a flat sheet, the adjustable containment shield may alternatively maintain a three-dimensional shape. In such embodiments, the three-dimensional shape may be conical, trapezoidal, or have some other non-flat design. Such optional embodiments may possess many of the aforementioned traits including, but not limited to, rigidity and transparency.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although there have been described particular embodiments of the present invention of a new and useful adjustable containment shield, it is not intended that such references be construed as limitations upon the scope of this invention except as set forth in the following claims.

What is claimed is:

1. An adjustable containment shield operable to mount on an output housing of a surgical instrument, the containment shield comprising:
    a substantially transparent body including:
    a distal face;
    a proximal face opposite the distal face;
    a generally consistent thickness defined between the distal face and the proximal face such that the body is pliable and resilient;
    a mounting hole defined in the body and operable to engage the output housing of the surgical instrument;
    a plurality of folds configured to allow the containment shield to move from a retracted position to an expanded position;
    the body further comprises an outer edge and a plurality of facets defined on the proximal face, each facet bounded by respective folds and the outer edge;
    at least one facet is configured to pivot relative to the mounting hole such that the containment shield moves from the retracted position to the expanded position; and
    when mounted on the output housing of the surgical instrument, the distal face is at an acute angle with respect to a longitudinal axis through the mounting hole and facing toward a patient engagement end of the surgical instrument while the proximal face is at an obtuse angle with respect to the longitudinal axis and facing toward a housing side of the surgical instrument.

2. The adjustable containment shield of claim 1, wherein the body further comprises a plurality of accordion sections, each accordion section including alternating adjacent folds of the plurality of folds, such that the at least one facet may pivot relative to the mounting hole.

3. The adjustable containment shield of claim 2, wherein the body further comprises two accordion sections.

4. The adjustable containment shield of claim 2, wherein the body further comprises four accordion sections.

5. The adjustable containment shield of claim 1, wherein:
    the plurality of facets includes insert facets; and
    the plurality of facets form guides, each guide configured to slidably receive a respective insert facet of the plurality of facets, such that the at least one facet may pivot relative to the mounting hole.

6. The adjustable containment shield of claim 1, further comprising a package, wherein the plurality of folds in the body of the containment shield enable the package to maintain the containment shield substantially flat within the package and wherein the containment shield is sterile within the package.

7. The adjustable containment shield of claim 1, wherein the containment shield further comprises a collar operable to connect the mounting hole of the body to the output housing of the surgical instrument.

8. The adjustable containment shield of claim 1, wherein the body further comprises a plurality of slits therethrough, each slit of said plurality of slits extending radially from a center point of the mounting hole.

9. The adjustable containment shield of claim 1, wherein the body further comprises a plurality of slits therethrough, each slit of said plurality of slits extending perpendicularly from an edge of the mounting hole.

10. The adjustable containment shield of claim 1, wherein the body further comprises a reflection reducing coating.

11. The adjustable containment shield of claim 1, wherein the mounting hole is operable to receive a shaft of the surgical instrument, and wherein the containment shield further comprises a removable layer of film on the distal face of the body, wherein the removable layer of film comprises a peel tab protruding from an edge of the body.

12. The adjustable containment shield of claim 1, wherein:
 the mounting hole has a diameter of approximately one half of an inch or larger; and
 the body further comprises a plurality of slits therethrough, each slit of the plurality of slits extending from an edge of the mounting hole, wherein each slit has a length of approximately one half of an inch.

13. A method of using an adjustable containment shield operable to mount on an output housing of a surgical instrument, the method comprising:
 (a) forming the containment shield into a three-dimensional shape including a distal face and a proximal face;
 (b) engaging a mounting hole of the containment shield onto the output housing of the surgical instrument such that the distal face is at an acute angle with respect to a longitudinal axis through the mounting hole and facing toward a patient engagement end of the surgical instrument while the proximal face is at an obtuse angle with respect to the longitudinal axis and facing toward a housing side of the surgical instrument; and
 (c) pivoting a facet of the containment shield relative to the mounting hole, thereby moving the containment shield from a retracted position to an extended position.

14. The method of claim 13, wherein step (c) includes extending a plurality of accordion sections.

15. The method of claim 13, wherein step (c) includes sliding an insert facet relative to a respective guide.

16. The method of claim 13, further comprising:
 removing a removable layer of film from the distal face, wherein the removable layer of film includes a peel tab protruding from an edge of the distal face.

17. The method of claim 13, further comprising:
 removing the containment shield from packaging, wherein the containment shield comprises a body that is substantially transparent and has a generally consistent thickness such that the body is pliable and resilient, wherein the body is substantially planar when in the packaging.

18. The method of claim 13, wherein step (a) includes creating a plurality of folds configured to allow the containment shield to move from the retracted position to the expanded position.

19. The method of claim 13, further comprising:
 pivoting the facet of the containment shield relative to the mounting hole, thereby moving the containment shield from the extended position to the retracted position.

\* \* \* \* \*